United States Patent [19]

Righelato et al.

[11] 4,130,461

[45] Dec. 19, 1978

[54] CONTINUOUS PROCESS FOR THE PRODUCTION OF POLYSACCHARIDE UNDER PHOSPHATE LIMITING CONDITIONS

[75] Inventors: Renton C. Righelato; Lynda Deavin, both of Reading, England

[73] Assignee: Tate & Lyle Limited, London, England

[21] Appl. No.: 798,762

[22] Filed: May 20, 1977

[30] Foreign Application Priority Data

May 28, 1976 [GB] United Kingdom ............... 22318/76

[51] Int. Cl.$^2$ ............................................. C12D 13/04
[52] U.S. Cl. .................................. 195/31 P; 195/115; 195/117
[58] Field of Search ................ 195/31 P, 115, 96, 117

[56] References Cited

U.S. PATENT DOCUMENTS

| 2,822,319 | 2/1958 | Monod | 195/115 |
|---|---|---|---|
| 3,856,625 | 12/1974 | Imrie | 195/31 P |

FOREIGN PATENT DOCUMENTS 1331771  9/1973  United Kingdom ................... 195/31 P

OTHER PUBLICATIONS

Neijssel et al., "The Regulation of Carbohydrate Metabolism in *Klobsiella aerogenes* NCTC418 Organisms, Growing in Chemostat Culture; *Arch Microbiol.* vol. 106, (1975), pp. 251–258.

Williams et al., "Exopolysaccharide Production by Pseudomonas NCIB 11264 Grown in Continuous Culture", *J. Gen. Micro.* vol. 104, (1978), pp. 47–57.

*Primary Examiner*—Thomas G. Wiseman
*Attorney, Agent, or Firm*—Ostrolenk, Faber, Gerb & Soffen

[57] ABSTRACT

Polysaccharide is produced in high yields by continuous culture of a polysaccharide-producing strain of *Azotobacter vinelandii* under phosphate-limited conditions, preferably with restricted oxygen uptake.

5 Claims, No Drawings

CONTINUOUS PROCESS FOR THE PRODUCTION OF POLYSACCHARIDE UNDER PHOSPHATE LIMITING CONDITIONS

This invention relates to a process for the production of a polysaccharide. More particularly the invention relates to the production of an alginate-type polysaccharide by the cultivation of bacteria of the species *Azotobacter vinelandii.*

Alginic acid, a hydrophilic colloidal carbohydrate acid, is a variable block copolymer composed of D-mannuronic and L-guluronic acid units. Although alginic acid itself is practically insoluble in water, it can readily be solubilised by neutralisation with a suitable alkali. One of the outstanding characteristics of alginate solutions is their high viscosity at very low concentrations; and when certain divalent ions, such as calcium or magnesium, are added to solutions of alginate, gelation is induced. The unique physical properties of alginic acid and alginates give them a wide range of industrial applications as emulsifiers, stabilisers and thickeners. For example, in the food industry, they can be used as emulsion stabilisers for ice cream, as gelling agents for milk puddings, and thickeners for sauces, and as foam stabilisers for beer; in pharmaceuticals, they can be used as emulsifiers and thickeners for surgical soaps and lotions, as disintegrating and granulating agents for tablets, as suspending agents for ointments, and as absorbable gels for surgical dressings; in paper and textile processing they can be used in sizing, coating, finishing, dyeing and printing compositions; and, in agriculture, they can be used as soil conditioners.

Alginates and alginic acid have been obtained on a commercial scale by extraction of certain species of brown seaweed, for example *Laminaria digitata* and *Ascophyllum nodosum,* in which they make up a large proportion of the cell walls.

This conventional seaweed extraction process suffers from the disadvantage of being dependent on the supply of alginate-containing seaweed as starting material. It is awkward to carry out because of the quantities of seaweed involved; and considerable further purification may be necessary, especially if food or pharmaceutical grade material is required.

In view of these difficulties, in recent years alginate-like polysaccharides have been produced by cultivation of several species of Azotobacter, in particular *Azotobacter vinelandii.* The alginic acid produced by this micro-organism is structurally similar to that obtained from seaweed, except that it is partially acetylated.

It is known that the production of polysaccharide using a strain of *Azotobacter vinelandii* is critically dependent on a number of factors, particularly the pH of the medium and also the level of phosphate in the medium.

U.K. patent specification No. 1,331,771, describes a process for the production of a polysaccharide consisting of a partially acetylated variable block copolymer of 1-4 linked D-mannuronic acid and L-guluronic acid residues which comprises cultivating a microorganism of the species *Azotobacter vinelandii* under aerobic conditions in an aqueous nutrient medium containing at least one monosaccharide and/or disaccharide as carbon source and containing as essential ingredients sources of molybdenum, iron, phosphate, magnesium, potassium, sodium, calcium and sulphate, under controlled pH conditions, such that the pH is maintained in the range of from 6.5 to 8.5 for at least the first half of the fermentation period and within the range of from 4.5 to 8.5 for the remainder of the fermentation period, if any, until a substantial formation of polysaccharide has occurred, and isolating the polysaccharide formed. The method of culture used in this process can be batch or continuous culture.

It is emphasized in that Specification that the level of phosphate in the growth medium plays an important role in effecting the yield of the polysaccharide. The Specification suggests that low phosphate levels improve the yield, a phosphate concentration of from 0.015 to 1.4 millimolar, preferably 0.2 to 0.7 millimolar being suggested. Under these conditions, polysaccharide concentrations of about 2.5 to 3.0 g/l are obtained.

In U.K. patent specification No. 1,394,413, a special selection of these conditions is described giving particularly good polysaccharide yields. In this Specification, a process similar to that of the earlier Specification is described and claimed, but limited in that the concentration of phosphate in the medium is from 0.1 to 0.8 millimolar, and that during the cultivation the pH of the medium is maintained within the range of 7.0 to 8.2. Using these conditions, polysaccharide concentrations of 3 to 3.5 g/l may be obtained.

U.K specification No. 1,394,413 again stresses that best results are obtained at low phosphate concentration.

We have now found that in continuous fermentation processes of this type, the actual concentration of phosphate present in the medium can, under certain conditions, be considerably higher than those emphasized in the earlier specifications.

Under continuous fermentation conditions, the essential requirement is that the culture is run under phosphate limited conditions. That is to say, it is the level of phosphate in the medium which becomes the determining factor in the concentration of the microorganism.

It will be understood that the concentration of cells of the microorganism present in the fermenter is a function of the concentration of phosphate which gives limiting conditions under continuous culture. The higher the phosphate concentration, the higher the concentration of cells present, when under limiting conditions. Provided this principle is followed, it is possible to produce phosphate limited conditions under continuous culture at phosphate levels considerably in excess of those disclosed in the earlier Specifications, and to obtain much higher polysaccharide concentrations, e.g. up to 27 g/l polysaccharide, particularly when using lower dilution rates.

According to the present invention, we provide a process for the production of a polysaccharide consisting of a partially acetylated variable block copolymer of 1-4 linked D-mannuronic and L-guluronic acid residues, which comprises subjecting to continuous cultivation a bacterium of the species *Azotobacter vinelandii* under aerobic conditions in an aqueous culture medium containing as essential ingredients at least one monosaccharide or disaccharide as carbon source and sources of phosphate, molybdenum, iron, magnesium, potassium, sodium, calcium and sulphate, said medium containing a fixed source of nitrogen and/or the aerating gas containing nitrogen, the concentration of phosphate in the medium being limiting on the concentration of the bacteria and being at least 1.0 millimolar, and during the cultivation, the pH of the medium being maintained within the range of 6.0 to 8.2.

Any strain of *Azotobacter vinelandii* can be used in the process of the present invention. However, particularly valuable strains which give especially good yields of the polysaccharide is that particularly mentioned in the two earlier Specifications and bearing the culture collection numbers NCIB 9068 and NCIB 8789, and that bearing the culture collection number NCIB 8660. These strains are available from the National Collection of Industrial Bacteria, Torry Research Station, P.O. Box 31, 135 Abbey Road, Aberdeen, Scotland, and are described in the Catalogue of the Collections.

The phosphate level used in the medium will, as indicated, vary depending on the cell concentration in the fermenter: the higher the cell concentration, the higher the phosphate level which is limiting. We have found, for example, that using a chemically defined medium of the type mentioned in Example 1 of the specification No. 1,331,771, a phosphate concentration of 1.0 millimolar at a dilution rate of 0.15 l/h is effectively limiting at a cell concentration of about 2.3 g/l. A phosphate concentration of 2.0 millimolar is effectively limiting at a cell concentration of about 4 g/l, while a phosphate concentration as high as 3.0 millimolar is effectively limiting at a cell concentration of about 4.7 g/l. At lower dilution rates, the cell concentration i.e. total cell mass at a particular limiting phosphate concentration increases, probably through an increase in individual cell weight. Thus, at a dilution rate of 0.05 l/h 3.0 mM phosphate is limiting at a cell concentration of about 14 g/l.

In any particular case, an indication of whether the phosphate concentration is truly limiting can be obtained by increasing the phosphate concentration and observing the effect on the cell concentration. If the concentration of a non-limiting component of the medium is raised, no significant change in the cell concentration is observed; however if the concentration of the limiting component is raised, the cell concentration rapidly responds by increasing. For example, increase of a limiting phosphate concentration two fold is found to produce at least a 10% increase in the cell concentration within 5 hours.

We have found that under conventional continuous culture conditions, for example those using a chemostat (see Herbert, Elseworth and Telling, 1956, Journal of General Microbiology, 14, 601), particularly advantageous phosphate levels are from 2.0 to 3.0 millimolar, giving a cell concentration of about 4 to about 4.7 g/l at a dilution rate of 0.15 $h^{-1}$ or about 14 g/l at 0.05 $h^{-1}$. Use of these levels has been found to give a polysaccharide concentration of up to about 27 g/l. No upper limit to the phosphate concentration can be set, except that dictated by the practical considerations governing the continuous fermentation process.

Said earlier specifications indicates that another factor which was important in the production of polysaccharide using *Azotobacter vinelandii*, is the amount of oxygen supplied to the fermentation system. Oxygen solution rates of about 5 to 50, preferably about 8 to about 20 millimoles of oxygen per liter of medium per hour are mentioned.

We have found that the efficiency with which the monosaccharide or disaccharide used in the medium is converted into polysaccharide is related to the rate of oxygen supply. In continuous culture conditions, the same is true of oxygen as of phosphate, in that it is the relationship of the oxygen level to the cell concentration which is relevant and not the oxygen concentration in the medium as such. We have shown that while an oxygen supply of about 50 millimoles per gram cell per hour gives under phosphate-limiting conditions a sucrose conversion of about 9%, an oxygen supply of from about 7 to about 22 millimoles/gram cell/hour can give a sucrose conversion of over 40%. An oxygen supply of 20.5 millimoles/gram cell/hour has in particular, been shown to give a sucrose conversion of about 49%.

The actual uptake of oxygen in millimoles per liter per hour corresponding to these figures will, of course, depend on the cell concentration in the fermenter. The uptake per liter per hour is generally within the ranges stated in the earlier Specifications, but it must be emphasized that it is the relationship of the oxygen supply to the cell concentration which is important.

Alteration of the supply of oxygen to the culture can be effected by various means. Firstly, the concentration of oxygen in the gas, usually air, which is passed into the culture during fermentation, can be altered by diluting the air with nitrogen or an inert gas, or by enriching the air with extra oxygen. Secondly, the pressure of the gas being passed into the culture can be altered so that the rate of dissolution is varied. Thridly, the efficiency with which the oxygen in the gas phase is transferred into the aqueous phase can be altered by altering the gas-liquid mixing characteristics, conveniently by altering the speed and efficiency of the stirrer. A combination of two or more of these methods can also be used to provide the correct balance of nitrogen and oxygen.

In order to produce polysaccharide at high rates and at a good efficiency of conversion of the mono- or disaccharide, it is necessary to control the growth rate of the bacteria and separately control the respiration rate so that the supply of oxygen to the bacteria is, on one hand not limiting, and on the other hand is not unnecessarily high. It must be emphasised that the oxygen supply must not be limiting as this lowers the production of polysaccharide. On the other hand, unnecessarily high respiration rates produced by high oxygen levels result in a large proportion of the carbohydrate source being oxidised to carbon dioxide, thus giving low conversion efficiencies.

The following Examples illustrate the invention further.

EXAMPLES 1-4

Four different media as shown in Table 1 were used:

The media were prepared and added to the cultures in two batches: Batch (1) was autoclaved at 1 kg/cm² for 1 hour in two parts which were combined aseptically after cooling. One part contained sucrose, $KH_2PO_4$ and $K_2HPO_4$ in 14 l, the other part contained $MgSO_4$, NaCl, and trace elements other than calcium and iron in 4 l. Batch (2) contained $CaCl_2$ and $FeCl_2$ in 2 l; the $CaCl_2$ was autoclaved in 1.9 l and the $FeCl_2$ was filter-sterilised in 100 ml and then added to the bulk of Batch (2). Batches (1) and (2) were added to the culture medium through separate lines, (1) being added at 9 times the rate of (2) so as to give concentrations in the culture as stated in Table 1.

TABLE 1

COMPOSITION OF GROWTH MEDIA

CONCENTRATION (g/l) [m.Molar]

| CONSTITUENT | Example 1 | Example 2 | Example 3 | Example 4 | Example 5 |
|---|---|---|---|---|---|
| Sucrose | 60 | 60 | 60 | 120 | 20 |
| $KH_2PO_4$ | 0.032 [1.0] | 0.064 [2.0] | 0.096 [3.0] | 0.096 [3.0] | 0.008 [0.25] |
| $K_2HPO_4$ | 0.12 | 0.25 | 0.38 | 0.38 | 0.032 |
| $MgSO_4 7H_2O$ | 1.6 | 1.6 | 1.6 | 1.6 | 0.2 |
| NaCl | 1.6 | 1.6 | 1.6 | 1.6 | 0.2 |
| $Na_2MoO_4$ | 0.008 | 0.008 | 0.008 | 0.008 | 0.008 |
| $CaCl_2 2H_2O$ | 0.34 | 0.34 | 0.34 | 0.34 | 0.043 |
| $FeCl_3 4H_2O$ | 0.017 | 0.017 | 0.017 | 0.025 | — |
| $H_3BO_4$ | 0.023 | 0.023 | 0.023 | 0.23 | — |
| $CoSO_4 7H_2O$ | 0.009 | 0.009 | 0.009 | 0.009 | — |
| $MnCl_2 4H_2O$ | 0.007 | 0.007 | 0.007 | 0.007 | — |
| $ZnSO_4 7H_2O$ | 0.009 | 0.009 | 0.009 | 0.009 | — |
| $CuSO_4 7H_2O$ | 0.0008 | 0.0008 | 0.0008 | 0.0008 | — |
| $FeSO_4 7H_2O$ | — | — | — | — | 0.003 |

Four continuous cultures of the chemostat type (Herbert et. al., ibid.) using *Azotobacter vinelandii* NCIB 9068 in a continuous culture apparatus with a culture volume of 1.0 liters, were each supplied with one of the sterile media as shown in Table 1, with the phosphate at the concentrations stated. The batches (1) and (2) were pumped into the culture at a combined rate to give the dilution rate stated in Table 2, and the culture broth over-flowed via a standpipe weir into a receiver vessel. The temperature was controlled as stated in Table 2.

The pH was controlled at 7.4 by automatic addition of 1M NaOH. Air was sparged into the fermenter at 1 liter/min, the impeller speed being adjusted so that oxygen uptake rates in the range 10–30 m moles/g cell/hour were obtained. Samples were taken from the fermenter at daily intervals and assayed for cell mass and polysaccharide concentration. To each 40 ml sample, 0.8 ml of 0.5 M EDTA plus 0.8 ml of 5 M NaCl was added. The samples were then centrifuged at 25,000 g for 40 mins. The cell pellet obtained was resuspended in distilled water, centrifuged at 25,000 g for 40 mins and the supernatant decanted. The pre-weighed tube containing the sediment was dried at 105° C. for 12 hours and weighed. The polysaccharide was precipitated from the supernatant of the first centrifugation by adding three volumes of propan-2-ol. The precipitate was collected by filtration, and dried in vacuo at 45° C. for 24 hours.

Phosphate limitation was obtained at phosphate concentration of 1.0 mM to 3.0 mM. Particularly useful concentrations of Polysaccharide were obtained using media containing 2.0 to 3.0 mM added phosphate.

EXAMPLE 5

Effect on polysaccharide yield of different aeration rates in the culture vessel, under phosphate limited conditions

*Azotobacter vinelandii* NCIB 9068 was grown on continuous culture using an aqueous culture medium having the composition shown in Table 1 in a stirred tank fermenter.

To the medium in the fermenter was added an inoculum grown on an agar slope, and fermentation was conducted in batch for 24 hrs at 30° C. and pH 7.5. A continuous medium feed was then supplied at a dilution rate of 0.15 $hr^{-1}$ (i.e. 150 ml/hr). Air was supplied to the culture at a rate of 1.7 l/min. The respiration rate of the organisms was varied by adjusting stirring rate, and allowing the culture to reach a "steady state". At each "steady state", polysaccharide production was measured by propan-2-ol precipitation followed by dry weight determination, cell product was measured by dry weight determination, and residual sucrose was measured by g.l.c. determination. The oxygen uptake was measured using a paramagnetic oxygen analyser and the $CO_2$ evolution using an infra-red $CO_2$ analyser.

After each steady state had been reached, 2 ml of sterile phosphate solution (0.125 M) was added to the culture vessel. In each case the concentration of bacteria increased, showing that the cell concentration had been limited by the phosphate concentration. The results are set out in Table 3.

TABLE 2

POLYSACCHARIDE PRODUCTION UNDER PHOSPHATE-LIMITED CONDITIONS

| Example | Phosphate concentration (m.M) | Dilution rate (d.r.) ($h^{-1}$) | Cultivation Temperature (°C) | Cell concentration (g/l) | Polysaccharide Concentration (p.c.) (g/l) | Polysaccharide Productivity = d.r. x p.c. (g/l/h) |
|---|---|---|---|---|---|---|
| 1 | 1 | 0.15 | 30 | 2.3 | 4.4 | 0.66 |
| 2 | 2 | 0.15 | 36 | 4.0 | 9.1 | 1.36 |
| 3 | 3 | 0.12 | 36 | 4.7 | 15.1 | 1.81 |
| 4 | 3 | 0.05 | 36 | 14 | 26.5 | 1.32 |

In each case, the phosphate concentration was shown to be limiting to the cell concentration by increasing the phosphate concentration 2 fold: within five hours the cell concentration was observed to have increased at least 10%

TABLE 3
EFFECT OF RESPIRATION RATE ON EFFICIENCY OF SUCROSE CONVERSION TO POLYSACCHARIDE

| Oxygen uptake (m moles/ g cell/ hour) | Cell concentration (g/l) | Polysaccharide concentration (g/l) | Sucrose used (g/l) | Sucrose to polysaccharide conversion | Stirrer speed (rev/min) |
|---|---|---|---|---|---|
| 7.0 | 0.5 | 0.70 | 1.65 | 42% | 400 |
| 12.4 | 0.42 | 0.84 | 1.8 | 47% | 500 |
| 20.5 | 0.44 | 1.09 | 2.2 | 49% | 600 |
| 28.2 | 0.44 | 1.16 | 4.7 | 25% | 700 |
| 51.0 | 0.69 | 0.89 | 9.9 | 9% | 870 |

From Table 3, it can be seen that the yield of polysaccharide from sucrose can be increased from 9% at higher aeration (and hence respiration) rates to 47–49% at oxygen uptake rates of between 12 and 20 m moles/g cell/hour.

We claim:

1. In a process for the production of a polysaccharide comprising subjecting to continuous cultivation a bacterium of the species *Azotobacter vinelandii* under aerobic conditions to allow an oxygen uptake in an aqueous culture medium containing as essential ingredients at least one monosaccharide or disaccharide as carbon source and sources of phosphate, molybdenum, iron, magnesium, potassium, sodium, calcium and sulphate, said medium being provided with a source of nitrogen selected from the group consisting of a fixed nitrogen source and gaseous nitrogen, and recovering the resulting polysaccharide the improvement which comprises maintaining the concentration of phosphate in the medium such that it limits the concentration of the bacteria and is at least 1.0 millimolar, and maintaining the pH of the medium during cultivation within the range of about 6.0 to about 8.2.

2. The process of claim 1, in which the strain of *A vinelandii* is selected from the group consisting of strains NCIB 9068 NCIB 8789 and NCIB 8660.

3. The process of claim 1, in which the concentration of phosphate in the medium is from about 2.0 to about 3.0 millimolar.

4. The process of claim 1, in which the oxygen uptake is restricted to a level giving optimum conversion of monosaccharide or disaccharide into polysaccharide.

5. The process of claim 4, in which the oxygen uptake is restricted to a level of about 7 to about 22 millimoles/g cell/hour.

* * * * *